(12) United States Patent
Simor et al.

(10) Patent No.: US 9,883,974 B2
(45) Date of Patent: Feb. 6, 2018

(54) DISINFECTING WOUND DRESSING AND PROCESS FOR PREPARING SUCH

(75) Inventors: Marcel Simor, Zoetermeer (NL); André Schilt, Houten (NL); Duurt Pieter Willem Alkema, The Hague (NL); Timo Huijser, Zoetermeer (NL)

(73) Assignee: NEDERLANDSE ORGANISATIE VOOR TOEGEPAST- NATUURWETENSCHAPPELIJK ONDERZOEK TNO, Delft (NL)

( * ) Notice: Subject to any disclaimer, the term of this patent is extended or adjusted under 35 U.S.C. 154(b) by 1167 days.

(21) Appl. No.: 13/518,666

(22) PCT Filed: Dec. 28, 2010

(86) PCT No.: PCT/NL2010/050893
§ 371 (c)(1),
(2), (4) Date: Sep. 14, 2012

(87) PCT Pub. No.: WO2011/081520
PCT Pub. Date: Jul. 7, 2011

(65) Prior Publication Data
US 2013/0046260 A1   Feb. 21, 2013

(30) Foreign Application Priority Data

Dec. 28, 2009 (EP) ..................... 09180792

(51) Int. Cl.
| | |
|---|---|
| *A61F 13/00* | (2006.01) |
| *A61L 15/46* | (2006.01) |
| *D06M 10/02* | (2006.01) |
| *D06M 16/00* | (2006.01) |
| *A61F 13/06* | (2006.01) |

(52) U.S. Cl.
CPC .. *A61F 13/00063* (2013.01); *A61F 13/00995* (2013.01); *A61L 15/46* (2013.01);
(Continued)

(58) Field of Classification Search
CPC .............. A61F 13/0063; A61F 13/0095; A61F 13/069; A61F 2013/00157;
(Continued)

(56) References Cited

U.S. PATENT DOCUMENTS 4,191,743 A    3/1980   Klemm
5,681,579 A *  10/1997  Freeman ............. A61F 13/0203
                                                          424/447
(Continued)

FOREIGN PATENT DOCUMENTS

DE    10 2004 050462 A1   6/2005
EP        0 298 726 A1    1/1989
(Continued)

*Primary Examiner* — Kim M Lewis
(74) *Attorney, Agent, or Firm* — Lucas & Mercanti, LLP

(57) ABSTRACT

A process for preparing a disinfecting wound dressing for the protection of wounds, such as burn wounds, ulcers and cuts, the process comprising the steps of providing a yarn-based substrate, subjecting a surface of the substrate to a plasma environment, thereby providing non-leaching and biocidal features to the substrate surface by exposing the substrate surface to an antimicrobial active compound reaction.

10 Claims, 2 Drawing Sheets

(52) U.S. Cl.
CPC .......... *D06M 10/025* (2013.01); *D06M 16/00* (2013.01); *A61F 13/069* (2013.01); *A61F 2013/0091* (2013.01); *A61F 2013/00157* (2013.01); *A61F 2013/00217* (2013.01); *A61F 2013/00238* (2013.01); *A61F 2013/00519* (2013.01); *A61F 2013/00931* (2013.01); *A61L 2300/404* (2013.01)

(58) Field of Classification Search
CPC .......... A61F 2013/00217; A61L 15/46; D06M 10/025; D06M 16/00
USPC .......................................... 602/41–43, 46–59
See application file for complete search history.

(56) References Cited

U.S. PATENT DOCUMENTS

| | | | | |
|---|---|---|---|---|
| 5,994,612 A | * | 11/1999 | Watkins | A41D 13/12 2/69 |
| 6,903,243 B1 | * | 6/2005 | Burton | A61F 13/0203 602/41 |
| 2002/0177828 A1 | * | 11/2002 | Batich et al. | 604/367 |
| 2004/0202700 A1 | | 10/2004 | Phaneuf et al. | |
| 2004/0247652 A1 | | 12/2004 | Sabesan | |
| 2008/0096001 A1 | * | 4/2008 | Emden | A41D 31/02 428/222 |
| 2011/0250253 A1 | * | 10/2011 | Cunkle | A01N 33/12 424/404 |

FOREIGN PATENT DOCUMENTS

| | | | | |
|---|---|---|---|---|
| EP | 1939350 A1 | * | 7/2008 | ............ A01N 33/12 |
| GB | 835927 A | | 5/1960 | |
| GB | 1390044 A | | 4/1975 | |
| GB | 2074029 A | * | 10/1981 | ............ A61L 15/24 |
| WO | 03/039602 A2 | | 5/2003 | |
| WO | 2009/071894 A1 | | 6/2009 | |

\* cited by examiner

DISINFECTING WOUND DRESSING AND PROCESS FOR PREPARING SUCH

CROSS-REFERANCE TO RELATED APPLICATIONS

This application is a 371 of PCT/NL 2010/050893, filed Dec. 28, 2010, which claims the benefit of European Patent Application No. 09180792.5, filed Dec. 28, 2009, the contents of each of which are incorporated herein by reference.

FIELD OF INVENTION

The invention relates to a disinfecting wound dressing for the protection of wounds, such as burn wounds, ulcers and cuts.

BACKGROUND OF INVENTION

The mortality of burn patients is 5%, the majority of which is caused by secondary infections. These infections are not only caused by the fact that burnt skin loses its ability to protect against micro-organisms, but also by the wound liquid produced by a burn wound, exudate, which provides an excellent breeding ground for micro-organisms. Existing wound dressings for burn wounds are complex and their application requires skilled medical personnel. One of the disadvantages of the known wound dressings is that they tend to stick to the wound, which causes wound trauma upon removal, and that they do not allow sufficient evaporation of water content from the exudate, which leads to their relatively fast saturation, which results in a patient discomfort. Moreover, wound dressings must be changed every day because of this fast saturation and in order to prevent infection of the wound.

Currently, there is no wound dressing concept available that sufficiently removes exudates, provides sustained protection against infection, causes no wound trauma upon removal, and can be used without changing for several days. For burn wounds there are several known treatment procedures. One of them includes applying a burn ointment or a burn cream like cerium nitrate-silver sulphadiazine cream directly on the wound, followed by a wound dressing application. Despite the healing potential of the cream, use of the cream together with a wound dressing is not widely applied, since there is no wound dressing available that can sufficiently transport a liquid, that can protect the wound from outside infections and that does not adsorb the cream before application of the cream has resulted in formation a protective layer on the wound. Therefore, in practice, the cream is not used together with a wound dressing unless necessary, like in the case of a face burn injury.

There are a few wound dressings known that possess antimicrobial activity. Those which are meant to be applied on a burn wound are mainly based on the presence of honey and silver. The standards set for honey in such an application are very high and the shelf life of such wound dressings is limited. The amount of released silver-ions—one of the most active substances against infection—is usually high and rises further with increased production of exudate. Moreover, as a drawback, silver promotes the adhesion of the wound dressing to a wound bed.

In order to provide a textile, which is a potential candidate for the production of a wound dressing, with antimicrobial (AM) properties, AM substances might be introduced either into the fibre bulk during the fibre production or onto the fibre surface in finishing processes. In the former case, antimicrobials are only physically incorporated within the polymer bulk and need to migrate onto the surface and be released in order to be effective. The limitation of this modification is thus the short term efficacy. Moreover, the release of antimicrobials to the environment might lead to the development of resistance of micro-organisms to the used antimicrobial compounds and may cause health problems.

Antimicrobials applied by finishing processes are either physically or covalently attached to the surface of textiles. Physically attached compounds are gradually released from the surface and are thus associated with the same problems as antimicrobials incorporated within the fibre bulk, i.e. they leach out of the dressing, which can yield environmental problems, especially in hospital settings, where spilled antimicrobial compounds can give rise to multi-resistant bacteria. Covalently attached antimicrobials show good durability and will not be released, which diminishes environmental problems.

There is no standard solution. The wound dressings that are used in burn centra stick to the dried cream, cannot be applied immediately after the cream application (there is 1-2 hours delay), do not provide any anti-microbial protection and get saturated very quickly. The cream usually needs to be re-applied every 8 to 24 hours.

SUMMARY OF INVENTION

It is an object of the invention to provide a disinfecting wound dressing for the protection of wounds, wherein the disadvantages identified above are reduced. In particular, the invention aims at obtaining a process for preparing a disinfecting wound dressing for the protection of wounds that is more apt in preventing colonization of micro-organisms in the wounds. Thereto, according to the invention, the process comprises the steps of providing a yarn-based substrate, and providing biocidal features to the substrate surface by exposing the substrate surface to an antimicrobial active compound reaction.

By applying a plasma to a yarn-based substrate and providing biocidal substances to the substrate surface, the growth and reproduction of micro-organisms is not only minimized, but the micro-organisms are very efficiently killed, thereby obtaining a wound dressing having an antimicrobial or biocidal coating. Further, the antimicrobial compounds does not leak anymore from the dressing, i.e. they are not liberated, but remain attached to the substrate, thus minimizing the risk of the induction of multi-resistance.

The term "wound dressing" applies to all material, generally a fabric or textile, which is directly placed upon a wound for protection of the wound against infection and mechanical damage and for absorbing exudate and debris from the wound. Also bandages, or other coverings that have these functions are regarded as wound dressing in the present invention.

The term "antimicrobial" or "biocidal" as used in this application is meant to refer to the ability to destroy at least some types of micro-organisms, inhibit development, growth or reproduction of at least some types of micro-organisms or inhibit their pathogenic action. Hence, it also includes a biostatic effect.

The term "plasma" as used in this application is meant to refer to a partially ionised gas that represents a chemically active environment, which consists of active species such as electrons, ions, radicals, metastables and photons. The term "surface" as used in this application is meant to refer to outer surfaces of a substrate, but also to outer surfaces of fibres in a substrate, inner surfaces of porous fibres in a substrate, and inner surfaces of pores in a substrate.

The term "textile" as used in this application is meant to refer to a thin, flexible material made of any combination of cloth, yarn, fibre, or polymer.

The term "cloth" as used in this application is meant to refer to a thin, flexible material made from yarns.

The term "yarn" as used in this application is meant to refer to a continuous strand of fibres. The term "fibre" as used in this application is meant to refer to a unit of matter, either natural, such as cotton, synthetic, such as polyester, or a combination thereof, which forms the basic element of, for example, fabrics, and textile structures. A fibre itself may have a porous structure with voids.

The invention also relates to a method for preparing such a disinfecting wound dressing.

In an advantageous embodiment according to the invention, the wound dressing includes a wound contact layer preventing substantial penetration of cream or ointment in the wound dressing and having the capability of non-sticking to a dried cream or ointment. Since the wound dressing does not allow the cream or ointment to penetrate in the wound dressing, it may be applied immediately after the application of the cream or ointment, so that a higher comfort for the patient can be obtained. Further, the wound dressing can hold the cream or ointment under such pressure that the patient can lie on an injured body part, thereby obtaining a higher comfort. In addition, due to the non-sticking feature of the wound contact layer, it does not stick to the dried cream, so that wound trauma on removal is prevented and the patient does not need to be, for example, showered for 15 minutes before the wound dressing removal as currently practiced. There is less pressure on a nurse as (s)he does not need to worry so much about damaging a healing skin. These characteristics are preferably introduced in the wound contact layer by the type of weaving or knitting structure that is used. A jersey structure is an example of this. Generally speaking, the pore size of the wound dressing layer should be small enough to prevent incorporation of the cream into the fabric structure. Nonetheless, the wound dressing can also be applied without application of cream or ointment, and it will have the advantageous property that it will also not stick to the wound itself.

In a further advantageous embodiment according to the invention, the wound dressing includes an absorbing layer placed on top of the wound contact layer. In contrast with known wound dressings, said wound dressing according to the invention handles very efficiently relatively big amounts of moisture produced by the wound and passing any applied layer of cream. Fluid can also be absorbed in the case no cream has been applied or when the wound fluid has passed through the cream layer due to e.g. cracking of the dry cream layer, i.e. when the wound fluid has got in direct contact with the wound dressing, the wound dressing can absorb much more wound fluid before getting stiff and soaked when compared to known wound dressings. In particular, the absorbing layer can be specifically arranged for absorbing water and/or exudate. Thus, the wound dressing according to the invention may prevent very well the potential leakage of the wound fluid. Thus, by having absorbing capacity, the wound dressing of the current invention minimizes the moisture that will be present in the interface of wound and wound cream and in the interface with the wound layer of the wound dressing.

By further including a water evaporation layer on top of the absorbing layer, the wound dressing advantageously tends to transport water or the wound fluid from the wound area to the exterior surface of the wound dressing facing away from the wound. The water evaporation layer can preferably be implemented by mechanically processing the yarn-based substrate from yarns composed of filaments having an "x", "v", "w", "y", hexachannel, or tetrachannel form, thereby improving the water evaporation performance significantly. An example of this technology for an increased water evaporation capacity of textiles is given by the technology that was designated as Coolmax®, where tetra-channels and hexachannels in the fabric are used to provide the evaporation characteristics (see e.g. http://www.coolmax-thermolite.com/coolmax.htm). The step of mechanically processing the substrate can be performed either prior to or after the step of subjecting the surface of the substrate to a plasma treatment.

The aspects disclosed above for the various layers can be combined into fewer layers. It is possible to make a layer which does not adhere to cream or ointment (because of the structure of the woven or knitted material) and which simultaneously comprises the antimicrobial compound. Further it is possible that the same layer also comprises the fluid absorbing and evaporation characteristics. Thus, the wound dressing may consist of four layers, three layers, two layers, or even one layer in which all these functionalities are combined.

Advantageously, the wound dressing includes a top layer provided with a structure preventing micro-organisms from entering the wound dressing, so that colonization of such micro-organisms on the wound bed is counteracted, also at dry circumstances. Optionally, the top layer is provided with an anti-microbial and non-leaching coating.

In combination with the anti-microbial features, the wound dressing can be used for a prolonged period of time. Overall, according to aspects of the invention, the wound dressing reduces the mortality in burn wounded patients, reduces patients discomfort and skin damage and reduces medical workload.

Currently, there is no cream that is advised to be used for a period longer than 48 hours. In principle, a wound dressing according to the invention can be used for a period longer than 48 hours, even with the cream or ointment applied without any need to frequently reapplication, thereby facilitating proper wound treatment in situations where the injured subjects are far away from hospitals (e.g. in battle field situations) or when a hospital capacity becomes limited, e.g. due to a relatively large amount of injured people such as in the event of a disaster.

Other advantageous embodiments according to the invention are described in the following claims.

BRIEF DESCRIPTION OF THE DRAWINGS

By way of example only, an embodiment of the present invention will now be described with reference to the accompanying figures in which.

DETAILED DSCRIPTON OF THE INVENTION

It is noted that the figures show merely preferred embodiments according to the invention. In the figures, the same reference numbers refer to equal or corresponding parts.

Figure 1:
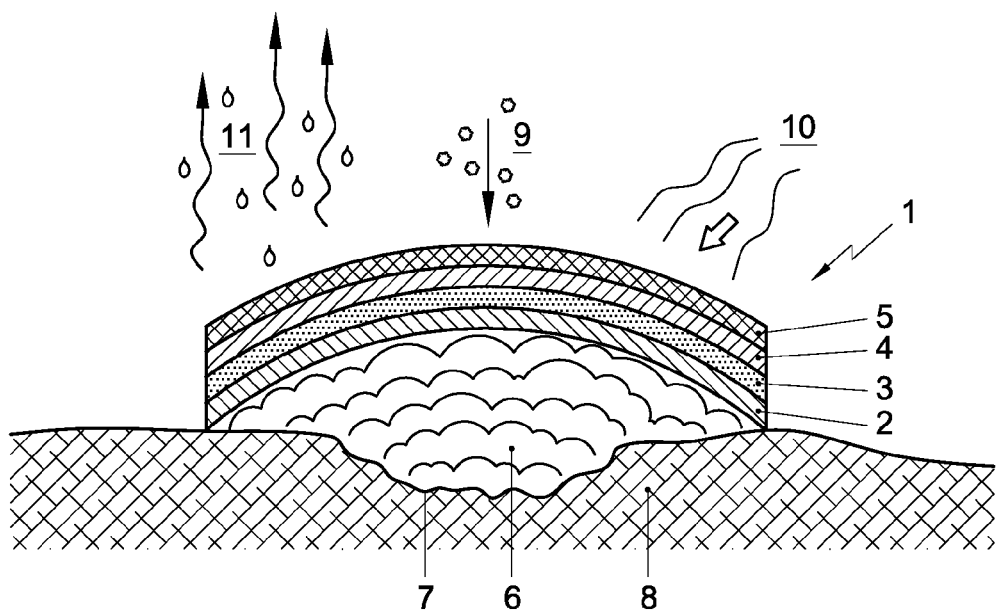
FIG. 1 shows a schematic cross sectional view of a wound dressing according to the invention.

FIG. 1 shows a schematic cross sectional view of a wound dressing 1 according to the invention. The wound dressing is intended for covering wounds, such as burn wounds, ulcers and cut wounds.

The wound dressing includes a multi-layer. In the shown embodiment, the wound dressing 1 includes four functional layers, viz. a wound contact layer 2, also called skin contact layer that e.g. prevents cream penetration, does not stick to dried cream, and assures easy transport of water in the case a cream was applied on a wound, or easy transport of wound fluid in other cases. The wound contact layer 2 forms the bottom layer that is applied to a wound surface 7 of a wound 8. The wound dressing further comprises an absorbing layer 3 that absorbs water coming from the cream layer through the wound contact layer 2 or exudate coming from a wound. The absorbing layer 3 is placed on top of the wound contact layer 2 for absorbing moisture. Then, the wound dressing comprises an evaporation layer 4 that promotes evaporation of water and/or the water content of the wound fluid stored in the absorbing layer 3. The evaporation layer 4 is placed on top of the absorbing layer 3. Optionally, the wound dressing further includes, as shown in FIG. 1, on top of the evaporation layer 4, a top layer 5 preventing micro-organisms 9 from entering the wound dressing and from reaching a wound and thus colonization on the wound bed. The top layer 5 can optionally contain a layer of nanofibres. More specifically, the top layer 5 can be composed of a nano fibre mesh. By a nanofibre, a fibre or filament is understood which is having either the diameter, in the case of circular-like cross-section, or at least one dimension, in the case of other than circular-like cross-section, in nanometer or sub-micrometer range. Optionally, the top layer 5 is provided with a substrate surface having non-leaching and biocidal features. It is noted that, in principle, layers can be integrated into a single layer. As an example, the absorbing layer 3 and the evaporation layer 4 can be integrated in a single layer. As a further example, all layers, except for the top layer, can be integrated into one layer.

The wound contact layer 2, the absorbing layer 3, the evaporation layer 4 and the top layer 5 prevent the colonization of microorganisms by absorbing (and evaporating the water content of) any wound exudate, biocidal action of the attached antimicrobial coating and by preventing entry of micro-organisms from the outside.

During use of the wound dressing 1, cream or ointment 6 can be present between the wound surface 7 and the wound contact layer 2. The cream or the ointment contains at least one topical anti-microbial agent such as silver sulphadiazine, zinc sulphadiazine, mafenide acetate, cerium nitrate, mupirocin, nystatin, gentamicin sulfate, povidone-iodine, bacitracin-polymyxin or nitrofurantoin.

The base material of wound contact layer 2, when in combination with the evaporation layer 4, is made of yarns which are made of filaments having a specific profile (X, Y etc.) by e.g. knitting. After production of such a dressing layer, the anti-microbial performance is provided by a plasma-assisted grafting of selected chemicals as has e.g. been described in WO 2008/082293.

The multilayer wound dressing 1 counteracts cream penetration into the wound dressing 1 immediately after the application of the cream 6 on a wound 8, even when a patient lies on the injured body part. The wound dressing 1 does also not stick to the dried cream, avoids wound trauma on removal, and can handle an eventual leak of exudates through the cream, sufficiently removes water vapour 11, provides sustained protection against infection, and can be applied on a wound for a prolonged period of several days. The wound dressing structure allows fresh air 10 entering the wound dressing 1.

The basic material used for the production of the wound dressing 1 is made of PP, PET, or other yarn filaments or combination thereof. Preferably, the yarns are mechanically processed, e.g. by weaving or knitting, to form e.g. the wound contact layer 2. The cream does not penetrate into the basic material due to a special weaving or knitting structure of the basic material like jersey etc. in a density that prevents the cream to penetrate the layer. Yarns are made of filaments of a special design providing the wound dressing with increased water vapour transmission, etc.

Figure 2:
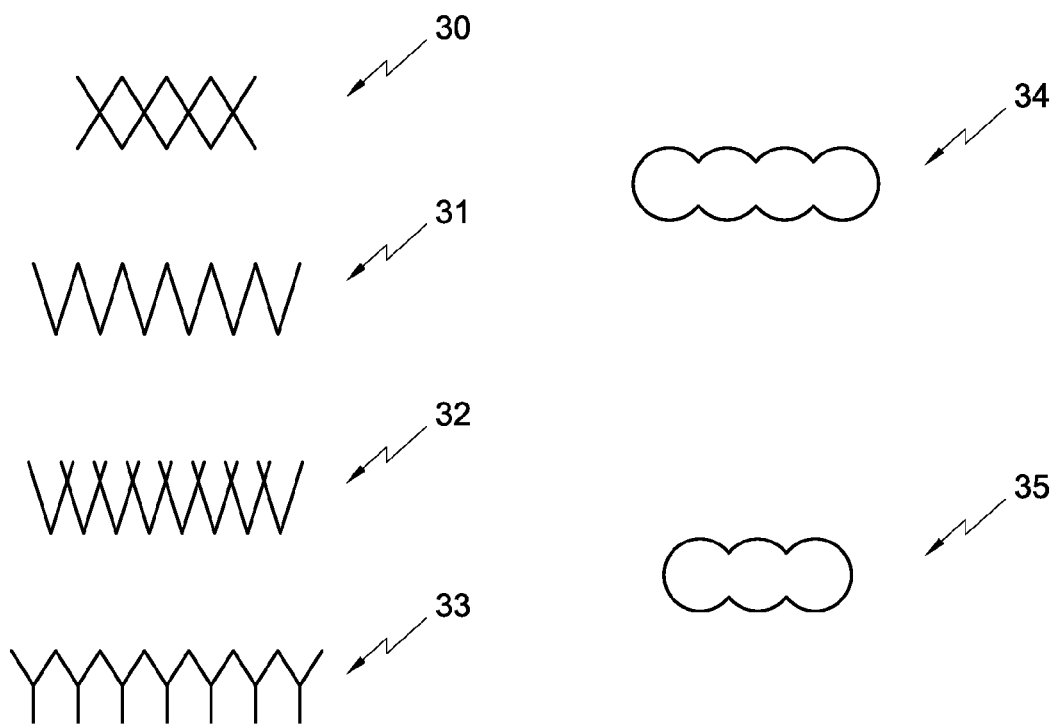
FIG. 2 shows a schematic detailed view of a yarn filament structure.

FIG. 2 shows a schematic detailed view of a yarn filament structure that can be used in the wound dressing of FIG. 1, specifically, "x" 30, "v" 31, "w" 32, "y" 33, hexachannel 34 or tetrachannel 35 formed shaped filaments. Fabrics properly designed from fibres composed of such yarns, i.e. according to the above described knitting or weaving technique, have the feature of preventing that (burn) cream penetrates into the wound dressing 1 and have the feature that the wound dressing does not or does hardly stick to dried cream 6 on the wound surface, and can handle an eventual leak of exudates through the cream 6. Apparently, also other profile filaments can be identified providing the substrate with the same or similar features.

The anti-microbial activity functionality can be obtained and improved by applying a plasma technology. In principle, also other functionality such as vapour transmission, absorption and/or anti-microbial activity can be improved by applying a plasma technology.

Figure 3:
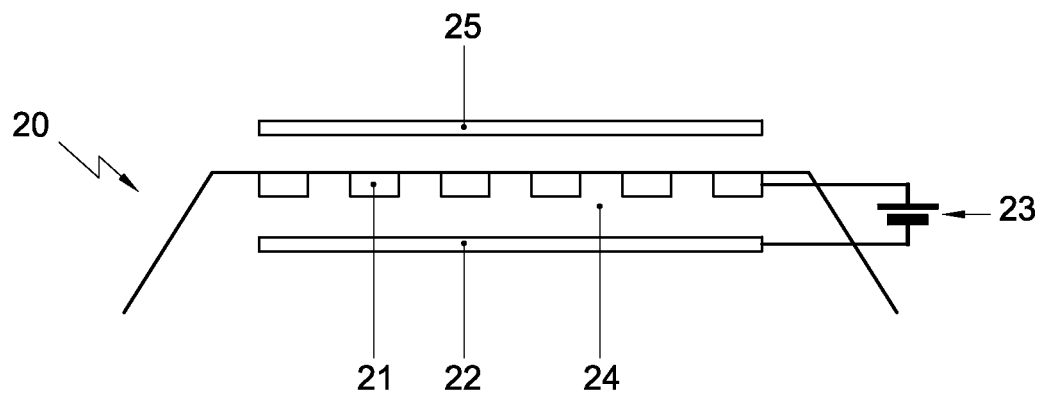
FIG. 3 shows a schematic cross sectional view of a surface dielectric barrier discharge for generating a plasma environment.

FIG. 3 shows a schematic cross sectional view of an example of a surface dielectric barrier discharge (surface DBD) 20 for generating a plasma environment. The surface DBD 20 includes a series of first electrodes 21 embedded in a dielectric slab 24 and a second ground electrode 22 that are interconnected via a power supply 23. Upon applying a potential differential over the electrodes 21, 22, a surface plasma environment can be generated on the surface of the dielectric slab 24. In the plasma environment, a substrate 25 is positioned for treatment. It is noted that both Surface and Co-planar surface DBD can be applied.

According to an aspect of the invention, the method is not limited to applying Surface DBD and/or Coplanar DBD plasma sources. Other plasma sources and techniques at atmospheric and/or low pressure can be applied. A non-exhaustive list includes for example APGD (atmospheric pressure glow discharge), volume DBD, microwaves discharge, micro-hollow cathode discharge and plasma jet source.

The protection against infection is provided by an anti-microbial coating on the surface of individual composing layers 2,3,4,5 or one or more layers combining the properties of these layers, and by the composition of layer 5. Methods of coating antimicrobial compounds onto fabrics are e.g. disclosed in WO 2008/082293. In a particular embodiment, the coating is applied by plasma-assisted grafting. The anti-microbial (AM) coating is permanent (i.e. no antimicrobial compound is released from the layer) and biocidal. The plasma-assisted grafting is a two-step process in which the plasma activation (an exposure of the surface of a material to plasma environment) is followed by the exposure to a precursor, e.g. a monomer. The monomer is then subjected to e.g. a conventional free radical polymerization on the activated surface. The unbonded chemical precursor is rinsed away.

In another embodiment, the coating is applied using other coating techniques like chemical vapour deposition or other grafting techniques like radical or ionic grafting, or UV-light induced grafting. As an example, in the activation grafting, gamma radiation, ultraviolet radiation, already mentioned discharges, electron beam radiation or other high energy radiation can be used as the energy source. The activation can be conducted as pre-irradiation of the substrate or as mutual irradiation of the substrate and the compound to be grafted. The purpose of the plasma activation is to introduce desirable chemical functional groups onto the treated surface before the second step of the plasma-assisted grafting. Those functional groups allow a) the selected chemical to be well bonded to a material which inherently does not have any/sufficient amount of bonding sites; b) improve AM functional characteristics of the coating compared to the case the selected chemical is deposit by another technique.

It is noted that a yarn-based substrate can be provided with desirable chemical functional groups in a number of other ways, for example, by chain-transfer activation, radiation or photochemical activation, and/or chemical activation.

Preferably, the antimicrobial active compound includes at least one of the group consisting of triclosan, triclocarban, chlorhexidine, chloroxylenol, chitosan acetate, zinc sulphadiazine, sodium dichloroisocyanurate and the antimicrobial active compounds comprising a quaternary ammonium moiety.

The plasma treatment is preferably performed at atmospheric pressure, preferably by surface DBD (Surface and/or Coplanar DBD and/or surface DBD jet). The selected AM chemical provides the desired non-leaching and biocidal AM performance. In this context it is noted that the non-leaching feature of compounds like triclosan, triclocarban, chlorhexidine and chloroxylenol is highly unexpected.

The non-leaching and biocidal features of the individual layers 2,3,4,5 provide for a protection against a wide variety of micro-organisms, such as bacteria, fungi and viruses. As an example, protection is obtained against gram-positive bacteria, such as *Staphylococcus aureus*, Coagulase-negative *Staphylococcus* species (e.g. *S. epidermis*), and *Enterococcus* species (e.g. *E. faecalis*), against gram-negative bacteria, such as *Pseudomonas aeruginosa, Acinetobacter* species (e.g. *A. baumannii*), *Klebsiella* species (e.g. *K. pneumoniae*), *Escherichia coli, Serratia marcescens, Proteus* species (e.g. *Proteus mirabilis*), *Enterobacter* species, *Bacteroides* species, against fungi: *Candida* species (e.g. *Candica albicans*), *Aspergillus* species, *Fusarium* species, *Alternaria* spp, *Rhizopus* spp, *Mucor* spp, and against viruses, such as Herpes simplex virus, Cytomegalovirus, Varicella-zoster virus.

Figure 4:
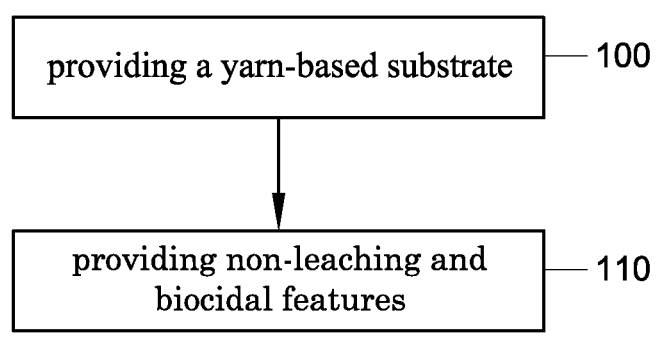
FIG. 4 shows a flow diagram of method steps according to the invention.

FIG. 4 shows a flow chart of method steps according to the invention. The method relates to a process for preparing a disinfecting wound dressing for the protection of wounds. The method comprises the step 100 of providing a yarn-based substrate, and the step 110 of providing non-leaching and biocidal features to the substrate surface by exposing the substrate surface to an antimicrobial active compound reaction.

By applying the wound dressing according to the invention, a number of advantages are obtained, viz. for a patient: a minimal chance of infection, and thus on all negative effects resulting from such an infection, much higher comfort (e.g. less wound dressing changes), and potential faster healing. For medical personnel the advantages are: a higher comfort (concerning changing of prior art wound dressings—two nurses might be occupied with one patient for several hours), less stressful work; and for a hospital: less risk of spread of antimicrobial compounds and hence less risk of the development of multi-resistant bacteria, lower mortality and lower costs per patient.

The invention is not restricted to the embodiments described herein. It will be understood that many embodiments are possible.

Other such embodiments will be apparent for the person skilled in the art and are considered to lie within the scope of the invention as defined in the following claims.

The invention claimed is:

1. A disinfecting wound dressing for the protection of wounds, such as burn wounds, ulcers and cuts, comprising:
   a yarn-based substrate layer composed of filaments of "x", "v", "w", "y", hexachannel, or tetrachannel form, having non-leaching and biocidal features, provided by exposing said substrate layer to a reaction with an antimicrobial active compound comprising
      subjecting the surface of the substrate to an environment resulting in either chain-transfer activation, radiation activation, photochemical activation, and/or chemical activation;
   a wound contact layer preventing the wound dressing from sticking to a wound, wherein said contact layer is combined with or identical to said substrate layer and wherein said combined substrate and contact layers also comprises absorbing and water evaporating properties.

2. The wound dressing according to claim 1, further including a top layer provided with a structure preventing micro-organisms from entering the wound dressing, and having non-leaching and biocidal features.

3. The wound dressing according to claim 1, wherein a top layer contains a layer of nanofibres.

4. The wound dressing according to claim 1, wherein the antimicrobial active compound includes a quaternary ammonium moiety.

5. The wound dressing according to claim 4, wherein the antimicrobial active compound is selected from the group consisting of triclosan, triclcarban, chlorhexidine, chloroxylenol, chitosan acetate, zinc sulphadiazine, and sodium dichloroisocyanurate.

6. A disinfecting wound dressing for the protection of wounds, such as burn wounds, ulcers and cuts, comprising:
   a yarn-based substrate layer composed of filaments of "x", "v", "w", "y", hexachannel, or tetrachannel form, having non-leaching and biocidal features, provided by exposing said substrate layer to a reaction with an antimicrobial active compound comprising subjecting the surface of the substrate to an environment resulting in either chain-transfer activation, radiation activation, photochemical activation, and/or chemical activation;
   a wound contact layer preventing substantial penetration of cream or ointment in the wound dressing and having a feature of non-sticking to a dried cream or ointment in the case cream or ointment is applied, wherein said contact layer may be combined with or identical to the substrate layer, and wherein said combined substrate and contact layer also comprises absorbing and water evaporating properties.

7. The wound dressing according to claim 6, further including a top layer provided with a structure preventing micro-organisms from entering the wound dressing, and having non-leaching and biocidal features.

8. The wound dressing according to claim 6, wherein the top layer contains a layer of nanofibres.

9. The wound dressing according to claim 6, wherein the antimicrobial active compound includes a quaternary ammonium moiety.

10. The wound dressing according to claim 9, wherein the antimicrobial active compound is selected from the group consisting of triclosan, triclcarban, chlorhexidine, chloroxylenol, chitosan acetate, zinc sulphadiazine, and sodium dichloroisocyanurate.

* * * * *